(12) United States Patent
Neuefeind et al.

(10) Patent No.: US 7,281,669 B2
(45) Date of Patent: Oct. 16, 2007

(54) APPARATUS AND METHOD FOR GENERATING A DEFINED ENVIRONMENT FOR PARTICLE-SHAPED SAMPLES

(75) Inventors: Torsten Neuefeind, Gauting (DE); Reiner Kiefersauer, Munich (DE); Holger Venzke, Nuremberg (DE); Martin Still, Nuremberg (DE)

(73) Assignee: Proteros Biostructures GmbH, Martinsried (DE)

( * ) Notice: Subject to any disclaimer, the term of this patent is extended or adjusted under 35 U.S.C. 154(b) by 302 days.

(21) Appl. No.: 11/035,769

(22) Filed: Jan. 13, 2005

(65) Prior Publication Data

US 2005/0183518 A1 Aug. 25, 2005

Related U.S. Application Data

(63) Continuation of application No. PCT/EP03/07606, filed on Jul. 14, 2003.

(30) Foreign Application Priority Data

Jul. 16, 2002 (DE) ................................ 102 32 172

(51) Int. Cl.
*F24F 11/00* (2006.01)
*F24F 3/14* (2006.01)
*G05D 22/02* (2006.01)

(52) U.S. Cl. .................... 236/44 C; 236/44 A; 165/223

(58) Field of Classification Search .............. 236/44 C, 236/44 A; 62/176.1, 91, 176.6, 92; 165/223, 165/229, 230; 378/80
See application file for complete search history.

(56) References Cited

U.S. PATENT DOCUMENTS 3,532,270 A 10/1970 Schoen, Jr. .................. 236/44

5,457,983 A 10/1995 Sauvageau et al. .............. 73/1
6,355,217 B1 3/2002 Kiefersauer et al. ........ 422/102
6,616,330 B2 * 9/2003 Nakamura et al. ............ 374/14

FOREIGN PATENT DOCUMENTS

| DE | 195 41 238 | 11/1995 |
| EP | 987 543 | 3/2000 |
| EP | 989 373 | 3/2000 |
| WO | WO 00/23795 | 4/2000 |

OTHER PUBLICATIONS

Kiefersauer, R. et al., Protein-Crystal Density by Volume Measurement and Amino-Acid Analysis, 1996, International Union of Crystallography.
Kiefersauer, R. et al., A Novel Free-Mounting System for Protein Crystals: transformation and improvement of diffraction power by accurately controlled humidity changes, 2000, International Union of Crystallography.
Sjogren, T., et al., Protein Crystallography in a Vapour Stream: data collection, reaction initiation and intermediate trapping in naked hydrated protein crystals, 2000, Journal of Applied Crystallography.

* cited by examiner

*Primary Examiner*—Chen-Wen Jiang
(74) *Attorney, Agent, or Firm*—Michael A. Glenn; Glenn Patent Group

(57) ABSTRACT

An apparatus for generating a defined environment for particle-shaped samples, comprises a support element with a rest end for a particle-shaped sample and an apparatus for generating a humid gas flow at a mouth end thereof. The mouth end is directed to the rest end. A gas provider provides gas having a first dew-point temperature. A cooler cools the gas to a cooler temperature under condensation of moisture to adjust a second dew-point temperature of the gas. A guide guides the gas with the second dew-point temperature to the mouth end, preventing condensation of moisture from the gas. A controller adjusts the relative humidity of the gas at the mouth end by adjusting the cooler temperature and adjusting the temperature of the gas at the mouth end.

24 Claims, 4 Drawing Sheets

APPARATUS AND METHOD FOR GENERATING A DEFINED ENVIRONMENT FOR PARTICLE-SHAPED SAMPLES

CROSS-REFERENCE TO RELATED APPLICATION

This application is a continuation of International Application No. PCT/EP03/07606, filed Jul. 14, 2003, which designated the United States and was not published in English and is incorporated herein by reference in its entirety.

BACKGROUND OF THE INVENTION

1. Field of the Invention

The present invention relates to apparatus and methods for generating a defined environment for particle-shaped samples, and in particular for particle-shaped samples having to be kept in an environment of defined humidity, such as protein crystals.

2. Description of the Related Art

The protein crystallography is a method of structural analysis of proteins in which these are exposed to X-ray or synchrotron radiation in order to explore the molecule structure from diffraction images. By the attachment of irregularly shaped proteins in a protein crystal, channels develop which are filled with crystallization solution. Protein crystals are very sensitive due to the high solvency content as well as by the weak contacts in comparison with crystals of small molecules and are only stable in a special environment.

In order to guarantee such a stable environment, previously protein crystals, together with some mother liquor, i.e. the solution in which the crystal has grown, are mounted in a glass capillary, which is then closed at both ends. Thus, in the capillary, an atmosphere arises, in which the crystal may be kept. This procedure, however, is disadvantageous, because it is a closed system, so that manipulations at the crystal are no longer possible. Furthermore, it is known to subject protein crystals to quick-freezing in a so-called loop representing a loop fixture and to measure same at low temperatures. Apart from temperature annealing, the crystal can also no longer be manipulated here.

Recently systems have become known, in which protein crystals are kept stable in a humid airflow, wherein by the adjustment of the humidity of the airflow the relative humidity at the crystal may be checked in a simultaneous analysis of the crystal state at an X-ray camera.

Such systems are known for example in Reiner Kiefersauer et al., "Free-mounting system for protein crystals: transformation and improvement of diffraction power by accurately control humidity changes", J. Appl. Cryst. (200), 33, pp. 1223-1230, and EP-A-0987543. These known systems include a measuring head including both a fixture for a protein crystal to be examined and a gas channel for feeding a humid air flow to the protein crystal. In these known systems, the humidity of the airflow is adjusted using a humidity regulation system, in order to adjust the mixing ratio of a dry airflow and a wet airflow depending on the humidity detected by means of a humidity sensor, in order to thus regulate the humidity of the airflow.

A similar method of adjustment of the humidity is also known in R. Kiefersauer et al., "Protein-Crystal Density by Volume measurement and Amino-Acid Analysis", J. Appl. Cryst. (1996), 29, pp. 311-317. In T. Sjögren et al., "Protein crystallography in a vapour stream: data collection, reaction initiation and intermediate trapping in naked hydrated protein crystals", J. Appl. Cryst. (2002), 35, pp. 113-116, there is also described a system for protein crystallography in a humid airflow. In this known system a bubbler is used to impart the gas with a desired humidity. In this, the gas is let to rise through a liquid, wherein the humidity of the gas may be manipulated by changing the temperature of the liquid or by changing the composition thereof. The gas with the humidity so adjusted is fed via a buffer vessel to a nozzle, at the outlet end of which a crystal is arranged at a fixture, so that a laminar gas flow strikes the crystal.

The known systems for adjusting the humidity of a gas flow are disadvantageous in that exact adjustment of the humidity, in particular in an interesting range slightly below 100% relative humidity, is difficult to realize therewith. In the methods mentioned first, using a humidity sensor, the employment of the sensor for the measurement of the relative humidity directly at the measurement location for the regulation of a humidifying means is not possible due to the spatial closeness at the crystal. Moreover, commercially available relative humidity sensors do not have sufficient accuracy and long-term stability in the required humidity range.

SUMMARY OF THE INVENTION

It is the object of the present invention to provide apparatus and methods for generating a defined environment for particle-shaped samples, which enable highly accurate and long-term-stable humidity conditioning at the location of a particle-shaped sample.

In accordance with a first aspect, the present invention provides an apparatus for generating a defined environment for particle-shaped samples, having a support element having a rest end for a particle-shaped sample; an apparatus for generating a humid gas flow at a mouth end thereof, wherein the mouth end is directed to the rest end, wherein the apparatus for generating the humid gas flow has a gas provider for providing gas having a first temperature and a first relative humidity, so that the gas has a first dew-point temperature; a cooler for cooling the gas to a cooler temperature under condensation of moisture to adjust a second dew-point temperature of the gas corresponding to the cooler temperature; a guide for guiding the gas with the second dew-point temperature to the mouth end, preventing condensation of moisture from the gas; and a controller for adjusting the relative humidity of the gas at the mouth end by adjusting the cooler temperature and adjusting the temperature of the gas at the mouth end.

In accordance with a second aspect, the present invention provides a method for generating a defined environment for particle-shaped samples, with the steps of supporting a particle-shaped sample at a rest end of a support element; generating a humid gas flow at a mouth end directed to the rest end, with the sub-steps of providing gas having a first temperature and a first relative humidity, so that the gas has a first dew-point temperature; cooling the gas to a cooler temperature under condensation of moisture in order to adjust a second dew-point temperature of the gas corresponding to the cooler temperature; guiding the gas with the second dew-point temperature to the mouth end, preventing moisture to condense from the gas; and adjusting the cooler temperature and the temperature of the gas at the mouth end for adjusting the relative humidity of the gas at the mouth end.

According to the invention, in order to achieve high required accuracy of the humidity values of a test gas, typically air, at the location of a particle-shaped sample, it is done without regulation of the humidity by means of a closed loop of humidifier and humidity sensor. Instead, the adjustment of the humidity according to the invention takes place via the precondition of the dew-point temperature without active humidity measurement. According to the invention, for the humidity adjustment of the dew point, a two-stage conditioning is employed, which takes place using a humidifying unit and a condensation unit in the form of a recooler. In the humidifying unit, the test gas is provided with a too high moisture by adjusting both dew-point and the temperature of the test gas to a value above the desired value. Thereafter, the gas is cooled again in the recooler, wherein excess water in the gas condenses again. Thus, the return-cooler temperature to which the gas is cooled sets the desired gas dew-point. The dew-point temperature corresponds to the gas temperature at which just 100% relative humidity is present in the gas, i.e. the gas is completely saturated, even minimal additional amounts of water can no longer be taken up by the gas. This state is achieved by the controlled condensation.

The so-conditioned test gas, typically air, is guided to the measurement head and takes on the desired gas temperature in the heat exchanger there. In order to prevent condensation of moisture therefrom while guiding the conditioned test gas to the measurement head, usually heated conduits holding the test gas above the cooler temperature are used. The temperature of the gas at the mouth end is controlled so that the humidity content of the measuring gas, expressed in relative humidity, results clearly by calculation from the quantities "dew-point temperature" and "gas temperature at the mouth end". Changes of the humidity content may now be adjusted by adjusting either the dew-point temperature, i.e. the cooler temperature, or the gas temperature at the mouth end correspondingly.

The connection between relative humidity $f_{rel}$, dew-point temperature $T_{dp}$ and gas temperature $T_g$ is given by the so-called Magnus formula. This reads:

$$F_{rel} = \exp\left\{a_w b_w \left[\frac{T_{dp} - T_g}{(b_w + T_{dp})(b_w + T_g)}\right]\right\} \times 100\%$$

With the constants $a_w$=17.50 and $b_w$=241.2 K.

The adjustment of the test gas temperature at the mouth end here preferably takes place by the adjusting of the temperature of a measuring head, through which the test gas is guided and which comprises the mouth end. The temperature of the measuring head may be adjusted by means of arbitrary known means, for example using heating windings, using Peltier elements, or using a liquid heat exchanger. Apart from heating the test gas in the measuring head, also cooling is possible by the employment of cooling aggregates, so that a further temperature range of the test gas may be adjusted. By cooling it is also possible to adjust very high humidities depending on the outside temperature.

According to the invention, preferably the temperature at the sample head and thus the gas temperature is controlled or regulated to a constant value, whereas the dew-point temperature, i.e. the return-cooler temperature, is varied corresponding to the desired humidity. Alternatively, the dew-point temperature may be held constant and the temperature of the sample head may be varied corresponding to the desired humidity.

In order to increase the accuracy of the adjustment of the relative humidity at the mouth end and thus at the particle-shaped sample, which is preferably arranged immediately at the mouth end, preferred embodiments of the present invention include means to compensate for the flow-through-dependent pressure loss in the gas conduit between the cooler and the mouth end in the adjustment of the relative humidity, i.e. the adjustment of the gas dew-point or the adjustment of the gas temperature at the mouth end.

In further embodiments, apart from the conditioning of temperature and humidity of the test gas, the inventive apparatus further enables mixing-in one or more additional foreign gases and/or a liquid converted to a gaseous state with a vaporizer. The apparatus comprises corresponding mass flow controllers in order to dose all fluid flows, i.e. measuring gas, foreign gases and/or liquid, so that from the ratio formation of the mass flows lowering or raising the dew-point adjusted in the recooler or the gas temperature at the mouth end may be calculated.

Instead of corresponding mass flow controllers, also other means for generating a defined flow or volume stream may be used, for example means containing pumps driven by a step motor in order to thereby cause a defined volume stream.

In the inventive apparatus and methods, the accuracy of the humidity adjustment does not depend on humidity sensors, but only on long-term-stable temperature sensors used for the adjustment of the gas temperature at the mouth end as well as for the adjustment of the cooler temperature, wherein these temperature sensors do not have to come into contact with the test gas directly. Thus, according to the invention, the disadvantages of relative humidity sensors do not occur, which consist in that in such sensors aging of the sensor material shifts the characteristic curve, that such sensors have poor accuracy in the range from 90% relative humidity to 100% relative humidity, that the aging mentioned is even more extreme in this range, and that humidity sensors with adequate accuracy are extremely expensive. Moreover, cheaper sensors mostly have only a limited measuring range. Dew-point probes also do not enable dew-point constancy in the range of one hundredth degree, whereas this may be guaranteed with the use of temperature probes as taking place according to the invention.

BRIEF DESCRIPTION OF THE DRAWINGS

These and other objects and features of the present invention will become clear from the following description taken in conjunction with the accompanying drawings, in which.

DESCRIPTION OF THE PREFERRED EMBODIMENTS

Figure 1:
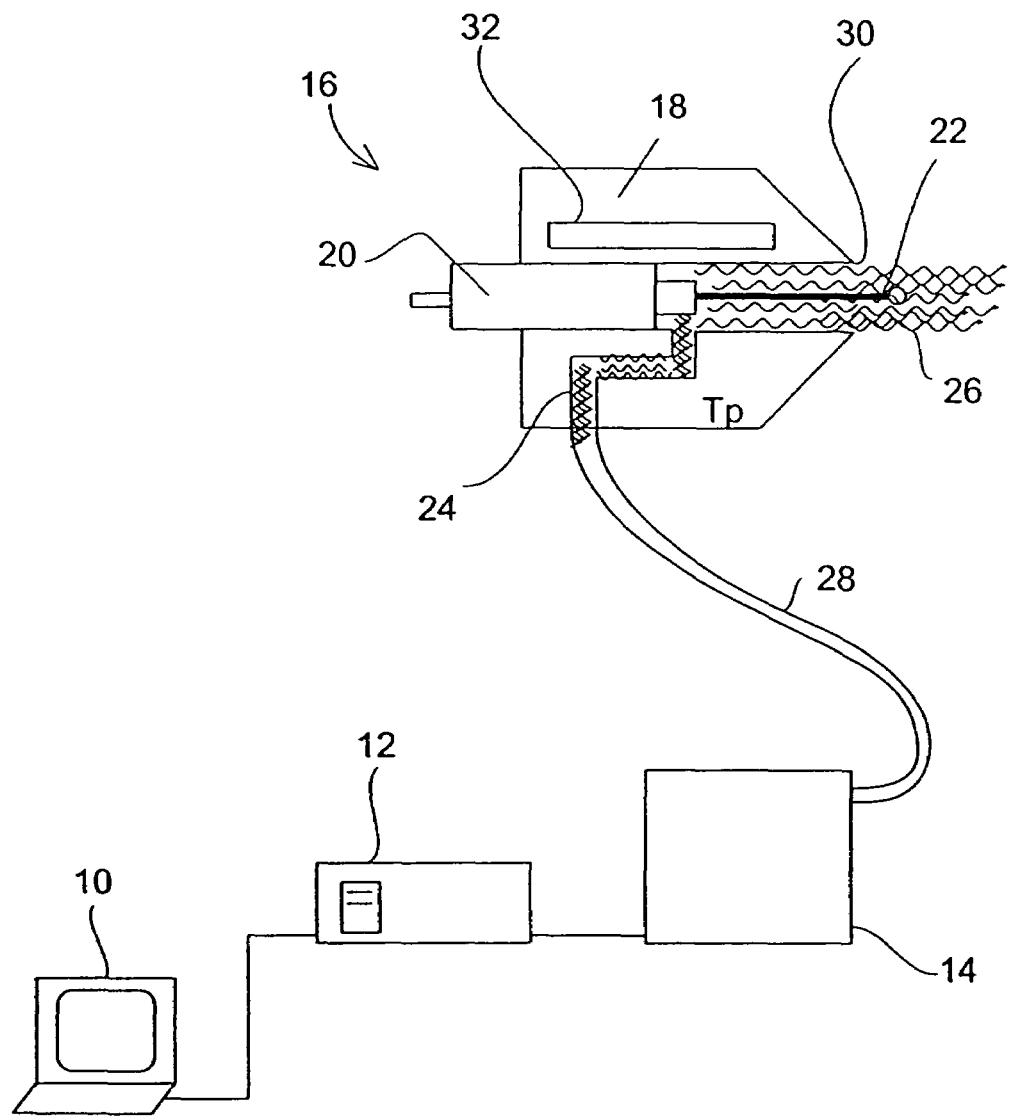
FIG. 1 is a schematic illustration of a system in which an inventive apparatus may be used.

FIG. 1 shows a system in which the present invention may find application, comprising a control computer 10, control electronics 12, a humidifying unit 14, and a sample head 16.

The sample head 16 may be a conventional sample head, as it is for example described in the above-mentioned EP-A-0987543. This sample head includes an outer part 18 and an inner part 20, which is preferably moveable with reference to the outer part 18. Attached to the inner part 20 is a support element 22 for supporting a particle-shaped sample, in particular a protein crystal. The present invention, however, is not limited to the use for particle-shaped samples in the form of protein crystals, but may be advantageously used for any particle-shaped samples having a high liquid content, i.e. having to be held in a humid environment. Among these are biological objects, such as biological cells or cell components, or also synthetic non-crystalline objects with high solvent content.

In FIG. 1 the support element 22 is illustrated as a loop fixture having a loop as rest end in which a protein crystal may be inserted. Such loop fixtures are known from the protein crystallography in particular for quick-freezing of samples. Alternatively, the fixture may include a hollow capillary (vacuum tweezers) operated with negative pressure or also a compact, elongated, tip-shaped component, at the end of which a rest for the particle-shaped material sample is given. In the inventive apparatus, any fixture devices are applicable, in which the particle-shaped sample may adhere at the rest end of a support element under the effect of absorption forces, electric forces, a glue material or the like.

As shown in FIG. 1, the sample head 16 further includes a gas channel 24, via which a humid airflow may be fed to the rest end of the support element 22 and thus the particle-shaped sample. Attached to the gas channel 24 is a gas conduit 28, via which the sample head 16 is connected to the humidifying unit 14. The humid gas flow 26 is guided under pressure from the humidifying unit 14 via the gas conduit 28 and the gas channel 24 to a mouth end 30 of the gas channel 24.

The rest end of the support element 22 is preferably immediately at the mouth end 30, wherein, however, a certain spacing, for example in the order of 1 to 10 mm, preferably 2 to 3 mm, is usually provided to enable simultaneous analysis of the crystal state using an X-ray camera.

Preferably, the gas channel 24 and the mouth end 30 thereof are formed to guarantee a substantially laminar gas flow 26 in the area of the rest end of the support element 22. To this end, it may be advantageous to provide the gas channel directly leading to the mouth end 30 without change of direction with a sufficient length. The flow rate of the humid airflow 26 is adjusted to support the generation of a laminar stream in the area of the rest end of the support element 22, wherein a good flow rate may be in the range of 0.6 to 2.0 l/min.

The sample head 16 further comprises tempering means 32 to adjust the temperature $T_p$ thereof. The gas channel 24 through the sample head 16 is embodied such that the humid airflow takes on the temperature $T_p$ of the sample head 16 when flowing through the sample head. To this end, the gas channel 24 may have a corresponding course or may for example also be embodied as several sub-channels. For adjusting the temperature of the sample head 16 also a temperature sensor (not shown) is provided thereat in a known manner.

The tempering means 32 may be an arbitrary known means for adjusting the temperature. In preferred embodiments of the present invention, the tempering means 32 is a liquid heat exchanger for sample head tempering enabling both heating and cooling the sample head 16. Thus, also gas temperatures below or close to the room temperature may be adjusted quickly. Alternatively, conventional Peltier elements or heating elements might be used for the adjustment of the sample head temperature and thus the humid airflow flowing through the sample head. At this point it is to be noted that in FIG. 1 only the gas conduit 28 is illustrated as the connection of the sample head to the rest of the system for clarity reasons, whereas further connections, for example electric connection lines, conduits for feeding a tempering fluid, conduits for feeding a vacuum for a supporting capillary and the like, are not shown.

The present invention is not limited to a sample head comprising a support element and a gas feed in combination. Rather, a support element and separately therefrom an apparatus directing a humid gas flow to the support element may be provided. Such an apparatus may for example have an elongated nozzle of sufficient length to support the generation of a laminar gas flow.

Before it is subsequently gone into the inventively used humidifying unit 14 in detail, it is to be pointed out briefly that all programming thereof for the performance of humidity experiments and the like may take place via the control computer 10 and control electronics 12. In the construction illustrated, control electronics 12 serve to feed the commands of the control computer 10 to the humidifying unit 14 as well as to the sample head 16. Since neither the control computer 10 nor the control electronics 12 are the subject matter of the present invention, they do not need to be explained further.

Figure 2:
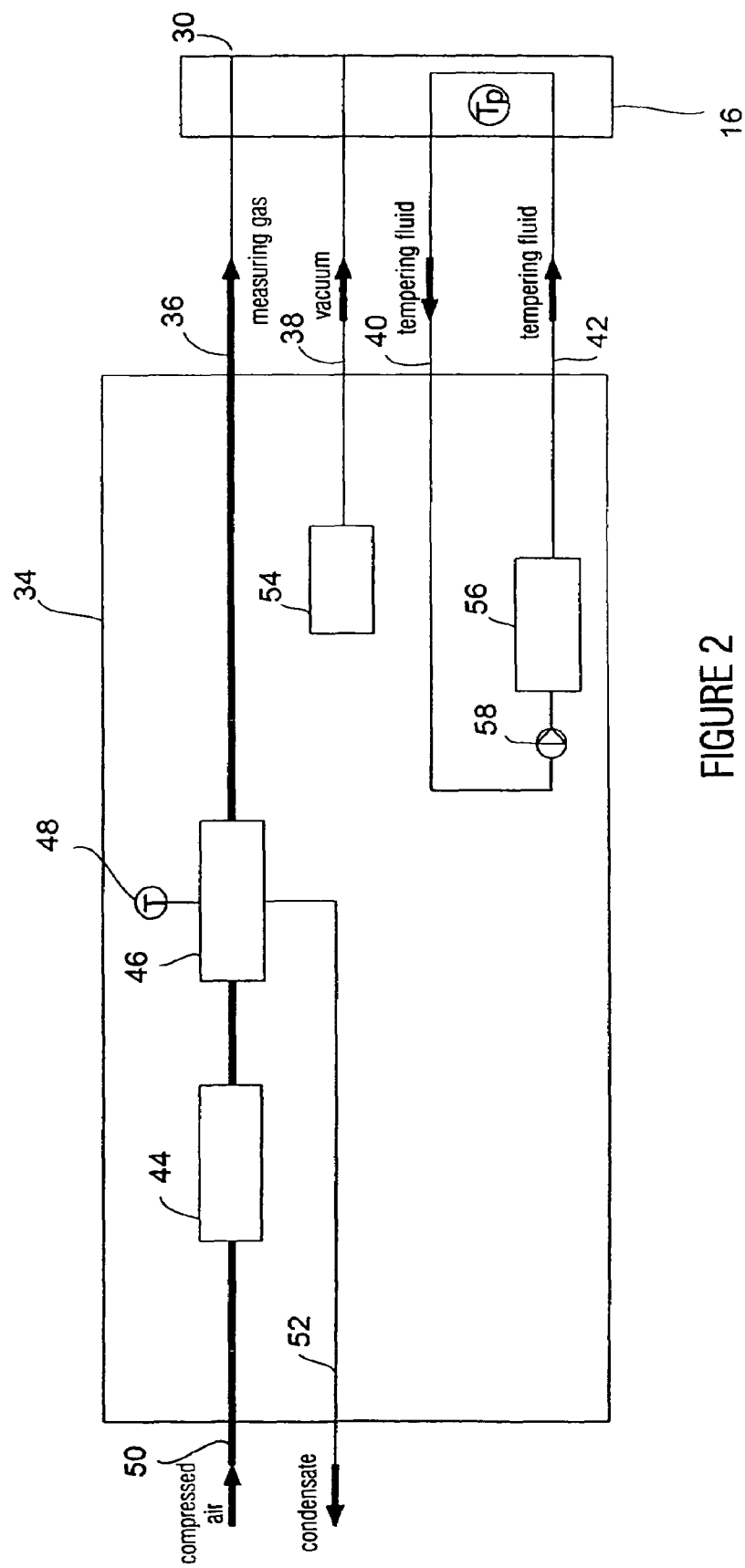
FIG. 2 is a schematic illustration of an embodiment of an inventive apparatus.

In the following, the embodiment schematically illustrated in FIG. 2 of an inventive apparatus for the generation of a defined environment for particle-shaped samples is explained in greater detail. It includes a fluid module 34 connected to the sample head 16 via a plurality of fluid conduits 36, 38, 40, and 42. Via the fluid conduit 36, the measuring gas is fed to the sample head and provided at the mouth end 30 thereof. The gas fed to the location of the particle-shaped sample, i.e. substantially the mouth end, to adjust the desired relative humidity is designated as measuring gas. As explained above, the measuring gas takes on the temperature $T_p$ of the sample head 16.

The humidifying unit for generating the humid gas flow guided through the fluid conduit 36 includes a humidifier 44 and a recooler 46. The recooler 46 has a temperature control means 48 for adjusting the cooler temperature of the recooler 46. The input of the humidifier 44 is connected to a compressed air conduit 50, whereas the output thereof is connected to the input of the recooler 46. The output of the recooler 46 is connected to the fluid conduit 36. The recooler 46 further has an output connected to a condensate conduit 52.

The fluid conduit 38 is connected to a vacuum pump 54 and also to a support capillary (not shown) provided in sample head 16, in order to hold a particle-shaped sample at the rest end of the support capillary.

The two fluid conduits 40 and 42 represent conduits for feeding and withdrawing a tempering fluid for adjusting the temperature of the sample head 16. To this end, these fluid conduits are connected in a known manner to a tempering control means 56 and a pump 58 for providing a tempering fluid flow through the tempering fluid conduits 40 and 42.

In the embodiment shown in FIG. 2, a gas flow of defined humidity at the mouth end 30 is generated as follows.

Depending on a humidity desired at the sample location and a default sample head temperature $T_p$, the dew-point temperature $T_{dp}$ required for the desired relative humidity $F_{rel}$ is determined, using the above-mentioned Magnus formula. This determination may take place in the control computer 10.

The cooler temperature is adjusted to the determined dew-point temperature $T_{dp}$, in order to thereby adjust the desired humidity at the location of the sample. For generating the gas flow with the dew-point temperature $T_{dp}$, at first compressed air imparted with a too high humidity in the humidifier 44, i.e. a dew-point at a temperature above the desired value, is fed to the humidifier 44 via the conduit 50. This too humid gas is fed to the recooler 46 and cooled to the cooler temperature $T_K$. Thereby excess water in the gas is condensed, so that the cooler temperature $T_K$ sets the desired gas dew-point and thus the dew-point temperature $T_{dp}$ of the measuring gas. The condensate generated in this is withdrawn via the conduit 52.

The measuring gas with the desired dew-point temperature $T_{dp}$ is guided to the mouth 30 under pressure in the above-described manner via the fluid conduit 36. In this, it has to be ensured that between the recooler and the measuring head 16 no condensation takes place, so that no reduction of the dew-point temperature can take place. To this end, the gas conduit 36 is preferably formed by a heated gas conduit, for example a flexible heated Teflon conduit. If it is ensured that the cooler temperature $T_K$ always lies below the ambient temperature in which the system is operated, the provision of a heating for the fluid conduit 36 is not required, because then it is ensured without providing a heating that the temperature of the measuring gas after leaving the recooler does not sink below the cooler temperature and thus condensation does not take place.

By inventively cooling the measuring gas starting from a higher temperature and humidity under condensation to a desired dew-point temperature $T_{dp}$, the dew-point temperature, i.e. the temperature at which the relative humidity at a given pressure is 100%, is exactly adjustable. After the recooler, each further condensation of moisture from the measuring gas is prevented. Thus, the relative humidity at the mouth end 30 and thus at the crystal only depends on the dew-point temperature of the measuring gas and the temperature of the measuring gas at the mouth end 30 corresponding to the above-referenced Magnus formula. In the given embodiment, the sample head 16 is regulated to a given temperature $T_P$ using the tempering fluid, so that the relative humidity of the measuring gas flow may be changed via an adjustment of the dew-point temperature of the measuring gas. This dew-point temperature of the measuring gas corresponds to the cooler temperature $T_K$, so that by adjusting the cooler temperature the relative humidity of the measuring gas at the mouth end 30 can be adjusted.

The described system enables the adjustment of the relative humidity at the mouth end of the sample head in an exact manner for the case that in the recooler and at the mouth end identical pressures prevail. Since this is very difficult to realize in practice, in preferred embodiments a correction means is provided to take pressure differences between the mouth end and the recooler into account.

For such a pressure correction, the vapor pressure curve of the pure substance system water/water vapor or ice/water vapor is used. This curve p(T) indicates the corresponding water vapor pressure p arising above a water or ice surface for each temperature T. For this curve, which is measured with high precision and which is about exponential in course, there are calculation equations.

Furthermore, it is started from the fact that in the mixture of humid air the water vapor fraction may thermodynamically be considered almost independent of surrounding gases (ideal gas mixture), so that the vapor pressure curve p(T) also applied for the water vapor partial pressure e(T) in the mixture. At a certain temperature T of the humid gas, not more than the water vapor partial pressure e(T) indicated by the vapor pressure curve can be present in the mixture.

In the recooling principle, air conditioned to a high humidity is cooled to a temperature $T_K$ and excess humidity condensed out. The water vapor partial pressure $e(T_K)$ arises in the gas, wherein the cooler temperature $T_K$ corresponds to the dew-point temperature $T_{dp}$ due to the recooling principle used.

In humid air, Dalton's law set up for ideal gases also applies, according to which the overall pressure of a mixture results from the sum of the partial pressures of the components, i.e. in humid air $p=p_{air}+e$. If the pressure of the gas mixture changes, all partial pressures change proportionately. This fact is taken into account in a correction for the compensation of the flow-through-dependent pressure loss in the measuring gas conduit 36.

For performing the inventive pressure correction, the pressure difference between the pressure in the recooler and the pressure at the mouth end has to be determined. As pressure at the mouth end or at the location of the sample a typical ambient pressure $p_P$ of 980 mbar may be assumed in a simplifying manner. Alternatively, to this end, an absolute pressure sensor may be provided at the sample head to detect the exact ambient pressure. Furthermore, the pressure $P_K$ present in the recooler 46 is detected by means of a pressure sensor, preferably a differential pressure sensor. The current pressure in the recooler $p_K$ varies depending on adjusted gas flow-through and temperature.

For the performance of the pressure correction, the accompanying dew-point temperature $T_{dp}$ is now determined from the desired relative humidity and the default sample head temperature via the above Magnum formula. From this dew-point temperature, the accompanying water vapor partial pressure $e_P$ is calculated via the vapor pressure curve. This can be directly calculated by the control computer or be determined by access to a look-up table.

From this determined partial pressure $e_P$ necessary at the sample head, the water vapor partial pressure $e_K$ to be adjusted in the recooler is determined corresponding to the ratio of the pressures in the recooler and at the location of the sample (ambient absolute pressure) as follows:

$$e_K = e_P \cdot \frac{P_K}{P_P}.$$

Via the vapor pressure curve, this water vapor partial pressure $e_K$ may again be converted to a dew-point temperature to be adjusted at the recooler. The recooler temperature $T_K$ is adjusted to this dew-point temperature to obtain the desired humidity at the location of the sample.

Thus, highly accurate adjustment of the humidity at the mouth end 30 may take place even at a pressure drop occurring across the measuring gas conduit 36.

Figure 3:
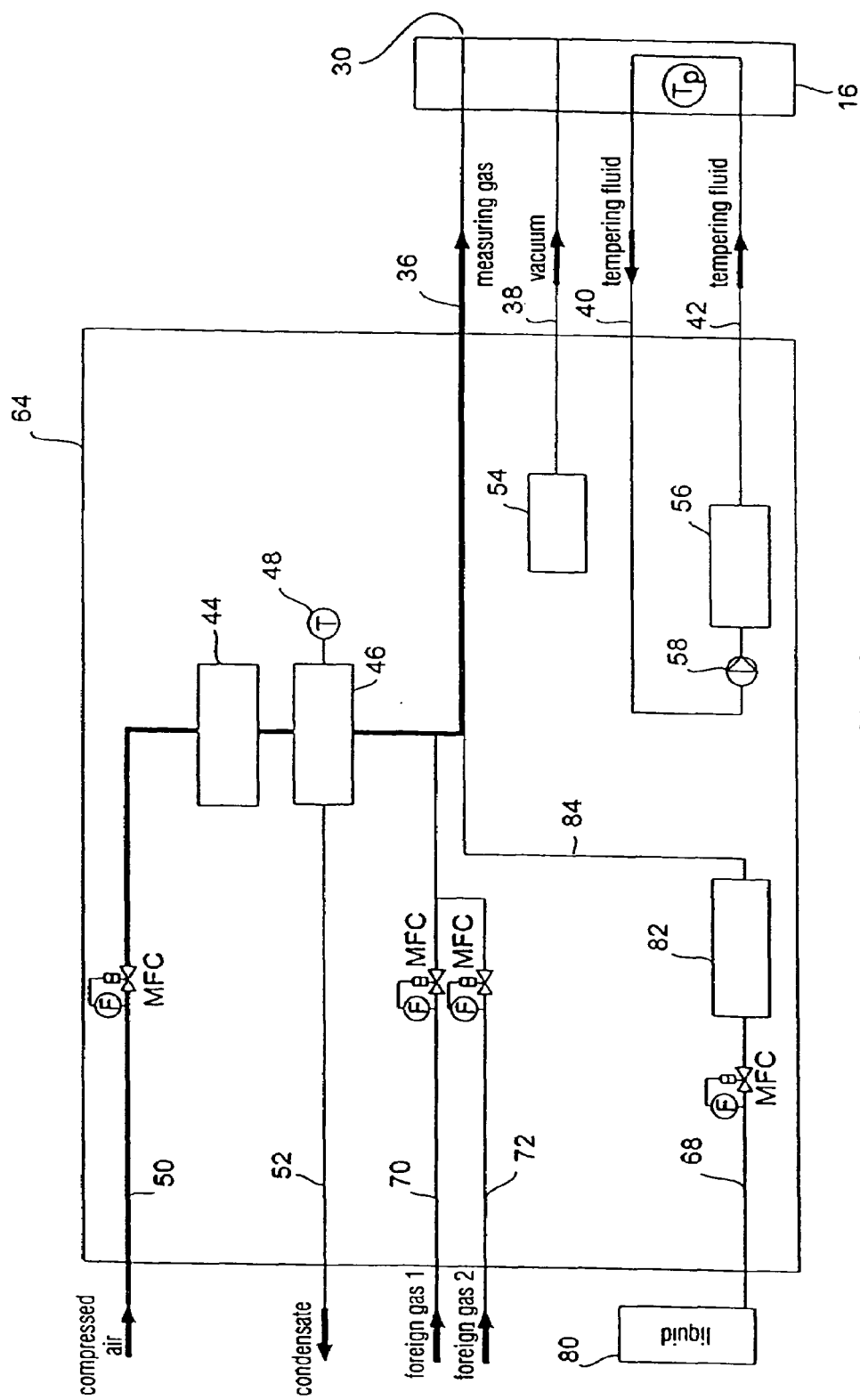
FIG. 3 is a schematic illustration of an alternative embodiment of an inventive apparatus.

Preferred embodiments of the present invention enable the addition of foreign gases and/or liquids into the measuring gas flow. A modified fluid module 64 provided with means required for this is shown in FIG. 3. To this end, foreign gas conduits 70 and 72 are connected to the measuring gas conduit 36 via respective mass flow controllers MFC. Via these conduits 70 and 72, a foreign gas 1 and a foreign gas 2 may be introduced into the measuring gas.

The system shown in FIG. 3 also enables introducing a vaporized liquid into the measuring gas. A liquid 80 may be fed via a liquid conduit 68, in which a mass flow controller MFC is provided, to a direct vaporizer 82 connected to the measuring gas conduit 36 via a gas conduit 84. The direct vaporizer causes residue-free vaporization of the liquid fed to it, so that the mass flow of the liquid fed to it corresponds to the gas leaving it.

Since in the system shown in FIG. 3 all fluid flows, both the measuring gas and the foreign gases 1 and 2 and the liquid are dosed via mass flow controllers, from the ratio formation of the mass flows, a lowering or raising of the dew-point adjusted in the recooler may be calculated, so that these may be taken into account in the adjustment of the humidity of the measuring gas at the mouth end 30. The liquid 80 fed may be a water-free liquid, for example isopropanol. If the liquid is not water-free, this has also to be taken into account in the adjustment of the humidity.

The present invention thus enables the arbitrary dosing-in of foreign gases or liquids via an internal vaporizer to the measuring gas, wherein the dosing of all fluids takes place via the mass flow controller MFC, so that the respective dosing-in may be taken into account in the adjustment of the humidity by correspondingly lowering or raising the dew-point adjusted in the recooler.

Figure 4:
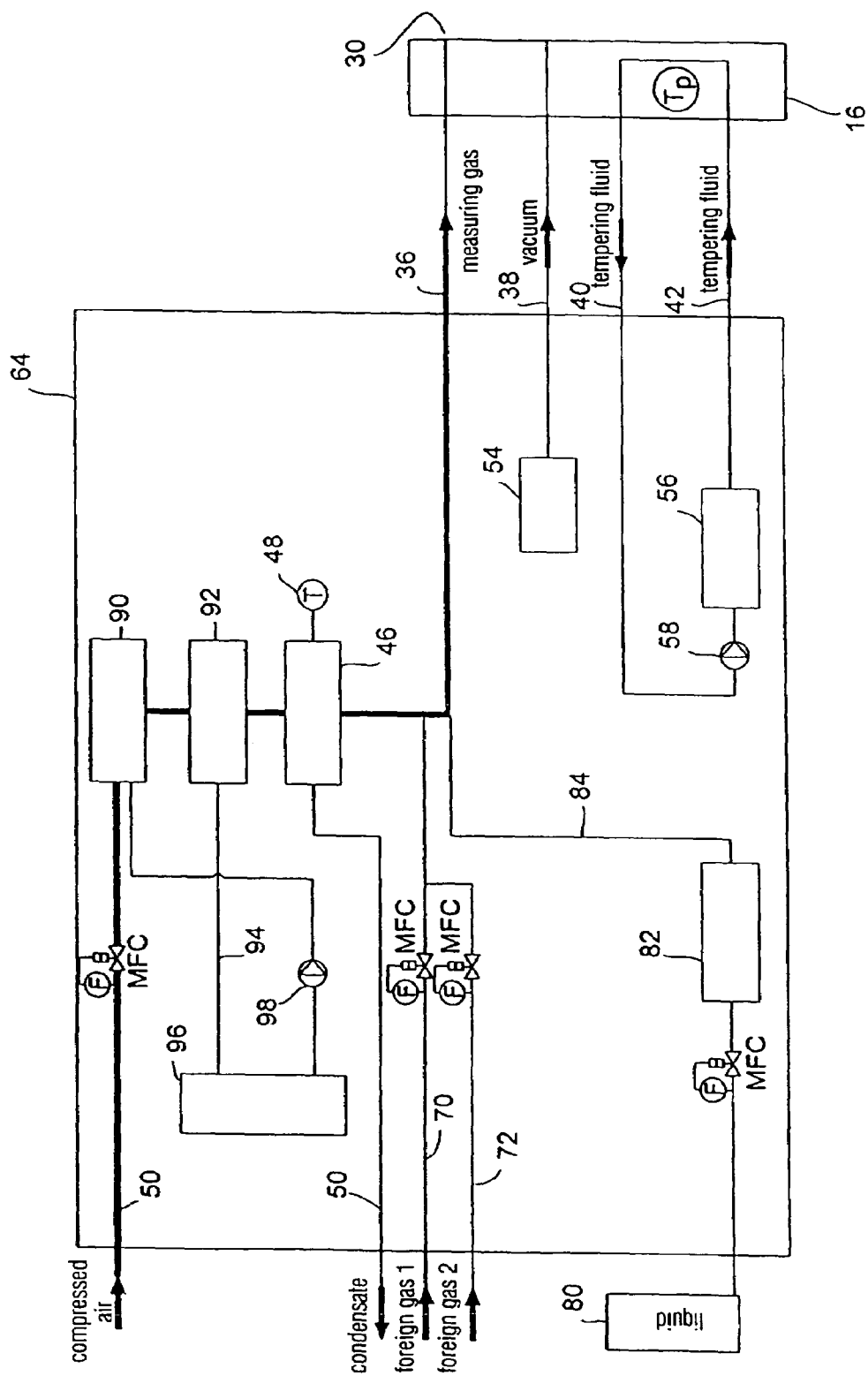
FIG. 4 is a schematic illustration of a further alternative embodiment of an inventive apparatus.

The inventively used humidifier for imparting the gas with increased humidity and increased temperature before it is subjected to recooling may be a conventional bubbler. An inventively preferred design of such a humidifier, however, is shown in FIG. 4. The humidifier is realized as a circulating humidifier comprising a humidifier unit 90 having an input connected to the compressed air conduit 50 and an output connected to an input of a separator 92. The output of the separator 92 is connected to the recooler 46. The separator 92 is also connected to a water supply 96 via a conduit 94. The water supply further comprises an output connected to a further input of the humidifier unit 90 via a pump 98. In the humidifier shown in FIG. 4, water from the water supply 96 is fed to the humidifier unit 90 via the pump 98, wherein the measuring gas, i.e. the compressed air, is humidified with the water in the humidifier 90. Liquid water is separated in the separator 92 and guided back to the water supply 96 via the conduit 94. A circulating humidifier as it is shown in FIG. 4 is advantageous as compared to an unwieldy bubbler since it may be embodied in a more compact manner.

The inventive apparatus and the inventive method enable highly exact adjustment of the humidity across a large range and in particular highly exact adjustment of the humidity in the interesting range for protein crystallography slightly below 100% relative humidity, for example between 80% and 100% relative humidity. According to the invention, particle-shaped samples may be examined at arbitrary temperatures, wherein only the corresponding gas temperature has to be adjusted correspondingly via the sample head temperature $T_P$. Depending on the temperature of the sample head, the dew-point temperature may be adjusted by correspondingly regulating the temperature of the recooler, to obtain a desired humidity. Advantageously, Peltier elements enabling increased stability of the temperature regulation may be used for this. Furthermore, by the use of recoolers with increased cooling power, an extended dew-point adjustment range is possible, wherein it is preferred to use a long gas path in the recooler, to obtain improved flow-through independence of the generated humidity values. Extended life of the recooler may also be achieved when it is embodied as a stainless steel recooler. The possibility of a highly flexible humidity adjustment and also the possibility of the examination of protein crystals at increased temperatures is provided by an exemplary adjustment range of the gas temperature of 5° C. to 60° C. and an exemplary adjustment range of the gas dew-point from 1° C. to 60° C.

The inventive apparatus is particularly suited for the application in the field of protein crystallography. It is known that by crystal shrinking the crystal order in protein crystals may be improved, wherein this process may be controlled directly via the water fraction in the crystal. As explained above, this water fraction may be controlled exactly by the present invention. Preferably, the control computer 10 as well as the control electronics 12 are formed to perform predetermined humidity experiments. The inventive apparatus may preferably comprise means enabling to adjust various parameters, such as starting value humidity, end value humidity and humidity gradient, selectively. Furthermore, the present invention may comprise means enabling to track the change of the crystalline order in X-ray during such humidity experiments.

An exemplary humidity experiment, which may be performed by the inventive apparatus for the generation of a defined environment for particle-shaped samples for example consists in at first mounting a protein crystal in its native state and then passing through a humidity ramp for the characterization of the crystal system. As a starting humidity the relative humidity of the native state may be chosen, whereas as an end humidity a humidity value is used which corresponds to the starting humidity minus 20%. The change in humidity may for example take place in steps of 0.25% each, so that with a humidity difference of 20% eighty humidity levels result. As dwell-time on a respective level, a time of 30 seconds may be implemented, so that the overall duration of such a humidity experiment would be 50 minutes. The reaction of a crystal to the humidity change may continuously be recorded with X-ray pictures.

While this invention has been described in terms of several preferred embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

What is claimed is:

1. An apparatus for generating a defined environment for particle-shaped samples, comprising:
   a support element having a rest end for a particle-shaped sample;
   an apparatus for generating a humid gas flow at a mouth end thereof, wherein the mouth end is directed to the rest end,
   wherein the apparatus for generating the humid gas flow comprises:
      a gas provider for providing gas having a first temperature and a first relative humidity, so that the gas has a first dew-point temperature;
      a cooler for cooling the gas to a cooler temperature under condensation of moisture to adjust a second dew-point temperature of the gas corresponding to the cooler temperature;
      a guide for guiding the gas with the second dew-point temperature to the mouth end, preventing condensation of moisture from the gas; and
      a controller for adjusting the relative humidity of the gas at the mouth end by adjusting the cooler temperature and adjusting the temperature of the gas at the mouth end.

2. The apparatus of claim 1, wherein the guide for guiding the gas comprises a fluid conduit and a measuring head having the mouth end, wherein the temperature of the fluid conduit and the measuring head is held at a temperature not falling below the second dew-point temperature.

3. The apparatus of claim 1, wherein the second dew-point temperature to be adjusted is determined on the basis of a desired relative humidity of the gas at the mouth end and a temperature to which the gas at the mouth end is adjusted.

4. The apparatus of claim 3, wherein the cooler temperature is adjusted to the determined second dew-point temperature and the temperature of the gas to the mouth end is adjusted to a constant value.

5. The apparatus of claim 1, wherein a pressure difference between a pressure in the cooler and a pressure at the mouth end is taken into account when adjusting the relative humidity at the mouth end.

6. The apparatus of claim 5, the pressure difference is determined based on a detected pressure in the cooler and a detected absolute pressure at the mouth end or based on a detected pressure in the cooler and a typical ambient pressure.

7. The apparatus of claim 6, wherein the second dew-point temperature to be adjusted is determined on the basis of a desired relative humidity of the gas at the mouth end and a temperature to which the gas at the mouth end is adjusted, by
   determining a dew-point temperature of the gas required at the mouth end on the basis of the desired relative humidity and the temperature of the gas at the mouth end;
   determining a required water vapor partial pressure of the gas at the mouth end from the temperature of the gas at the mouth end and the required dew-point temperature of the gas at the mouth end;
   determining a water vapor partial pressure required in the cooler based on the required water vapor partial pressure of the gas at the mouth end and the pressure difference; and
   determining the second dew-point temperature of the gas to be adjusted based on the determined required water partial pressure in the cooler.

8. The apparatus of claim 1, wherein the cooler temperature and the temperature of the gas at the mouth end are adjusted such that predetermined courses of the humidity of the gas flow are adjusted.

9. The apparatus of claim 1, further comprising a feeder for feeding one or more foreign gases to the humid gas flow.

10. The apparatus of claim 1, further comprising a direct vaporizer for feeding a vaporized liquid to the humid gas flow.

11. The apparatus of claim 8, wherein the change of the dew-point of the humid gas flow by the feeding of the one or more foreign gases and/or the feeding of the vaporized liquid is taken into account in the adjusting of the relative humidity at the mouth end.

12. The apparatus of claim 1, wherein the temperature for adjusting the temperature of a sample head comprising the mouth end is adjusted for adjusting the temperature at the mouth end comprises a second adjuster.

13. A method for generating a defined environment for particle-shaped samples, comprising:
   supporting a particle-shaped sample at a rest end of a support element;
   generating a humid gas flow at a mouth end directed to the rest end, comprising the following sub-steps:
      providing gas having a first temperature and a first relative humidity, so that the gas has a first dew-point temperature;
      cooling the gas to a cooler temperature under condensation of moisture in order to adjust a second dew-point temperature of the gas corresponding to the cooler temperature;
      guiding the gas with the second dew-point temperature to the mouth end preventing moisture to condense from the gas; and adjusting the cooler temperature and the temperature of the gas at the mouth end for adjusting the relative humidity of the gas at the mouth end.

14. The method of claim 13, further comprising the step of holding the gas with the second dew-point temperature after the cooling thereof to the cooler temperature at a temperature not falling below the second dew-point temperature.

15. The method of claim 13, further comprising a step of determining the second dew-point temperature to be adjusted on the basis of a desired relative humidity of the gas at the mouth end and a temperature to which the gas at the mouth end is adjusted.

16. The method of claim 15, wherein in the step of adjusting the temperature the cooler temperature is adjusted to the determined second dew-point temperature and the temperature of the gas at the mouth end is adjusted to a constant value.

17. The method of claim 11, further comprising a step of taking into account a pressure difference between a pressure present when cooling the gas to the cooler temperature and a pressure at the mouth end when adjusting the relative humidity.

18. The method of claim 17, wherein the step of taking into account a pressure difference comprises a step of determining the pressure difference based on a detected pressure in a cooler in which the gas is cooled to the second dew-point temperature and a detected absolute pressure at the mouth end or based on the detected pressure in the cooler and a typical ambient pressure.

19. The method of claim 18, further comprising a step of determining the second dew-point temperature to be adjusted on the basis of a desired relative humidity of the gas at the mouth end and a temperature to which the gas is adjusted at the mouth end, including the following sub-steps:

determining a dew-point temperature of the gas required at the mouth end on the basis of the desired relative humidity and the temperature of the gas at the mouth end;

determining a required water vapor partial pressure of the gas at the mouth end from the temperature of the gas at the mouth end and the required dew-point temperature of the gas at the mouth end;

determining a water vapor partial pressure required in the cooler based on the required water vapor partial pressure of the gas at the mouth end and the pressure difference; and determining the second dew-point temperature of the gas to be adjusted based on the determined required water partial pressure in the cooler.

20. The method of claim 13, wherein in the step of adjusting the cooler temperature and the temperature of the gas at the mouth end same are adjusted such that predetermined courses of the humidity of the gas flow are adjusted.

21. The method of claim 13, further comprising a step of feeding one or more foreign gases to the humid gas flow.

22. The method of claim 13, further comprising a step of feeding a liquid vaporized by means of a direct vaporizer to the humid gas flow.

23. The method of claim 21, further comprising a step of taking into account the change of the dew-point of the humid gas flow by the feeding of the one or more foreign gases and/or the feeding of the vaporized liquid when adjusting the relative humidity of the gas at the mouth end.

24. The method of claim 13, wherein the step of adjusting the gas temperature at the mouth end comprises a step of adjusting the temperature of a sample head comprising the mouth end.

* * * * *